United States Patent [19]

Anderson et al.

[11] Patent Number: 5,008,358

[45] Date of Patent: Apr. 16, 1991

[54] POLYMER COMPOSITIONS

[75] Inventors: Larry Anderson, Battersea; Gregory N. Batts; Malcolm D. Purbrick, both of Bushey; Clare E. Scriven, Harrow; Stephen A. Jones, Barnet, all of England

[73] Assignee: Eastman Kodak Company, Rochester, N.Y.

[21] Appl. No.: 571,617

[22] PCT Filed: Jan. 4, 1990

[86] PCT No.: PCT/GB90/00014

§ 371 Date: Sep. 4, 1990

§ 102(e) Date: Sep. 4, 1990

[87] PCT Pub. No.: WO90/07528

PCT Pub. Date: Jul. 12, 1990

[30] Foreign Application Priority Data

Jan. 6, 1989 [GB] United Kingdom ............... 8900221

[51] Int. Cl.$^5$ ................. C08F 12/16; C08F 22/00; C08F 20/18; C08F 222/18
[52] U.S. Cl. ................. 526/292.3; 526/292.95; 526/328; 526/329.4
[58] Field of Search ............ 526/292.95, 292.3

[56] References Cited

U.S. PATENT DOCUMENTS 4,016,133  4/1977  Hyosu et al. .............. 526/292.3

OTHER PUBLICATIONS

P. Bajaj and M. Padmanaban, Copolymerization of Acrylonitrile with 3-Chloro, 2-Hydroxy-Propyl Acrylate and Methacrylate, Journal of Polymer Sciences: Polymer Chemistry Edition, 21, 2261-2270 (1983).

Primary Examiner—Joseph L. Schofer
Assistant Examiner—Wu C. Cheng
Attorney, Agent, or Firm—Doreen M. Wells

[57] ABSTRACT

A hydrophilic crosslinkable copolymer comprising monomer units derived from an ester of an ethylenically unsaturated carboxylic acid wherein the ester group contains a labile primary hydroxyl group and monomer units derived from a halohydroxyalkyl ester of an ethylenically unsaturated carboxylic acid is disclosed. The copolymer is useful in affinity separation systems.

5 Claims, 2 Drawing Sheets

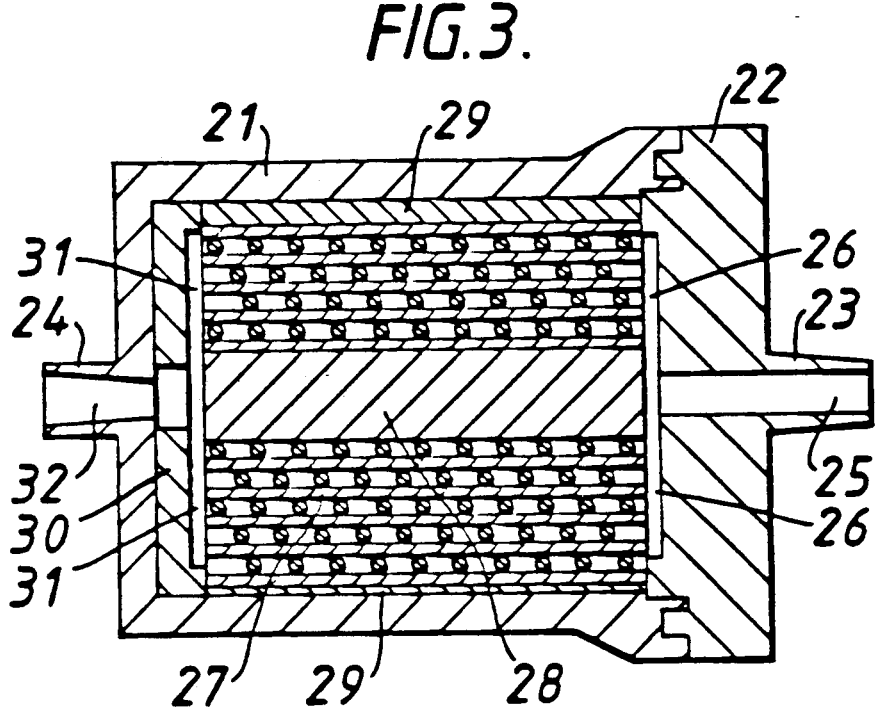
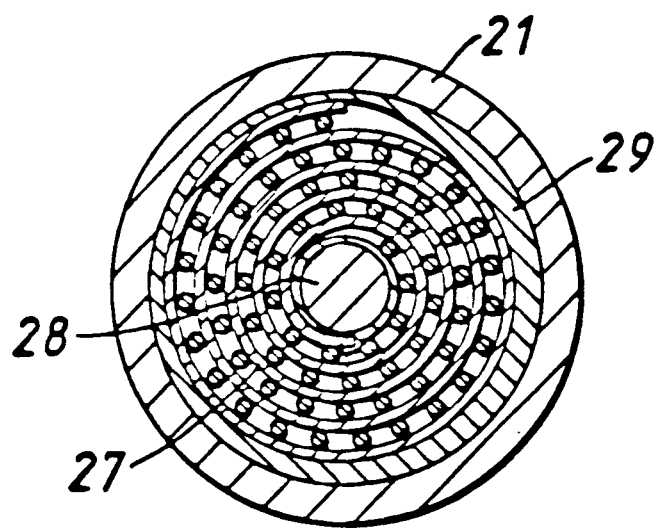

POLYMER COMPOSITIONS

The invention relates to polymer compositions particularly, but not exclusively, suitable for use in the preparation of supports for affinity chromatography.

Known polymeric supports include crosslinked labile hydroxy group-containing polymers. For example, U.S. Pat. No. 4,330,440 describes polymer supports for affinity chromatography comprising poly(hydroxyethyl methacrylate). The support is activated by reaction with a carbonylating agent to facilitate the coupling of a ligand to the support. The ligand is a substituent selected to be specifically interactive with a compound to be immobilised on the polymer support. For example, the ligand may be a protein.

A number of crosslinking agents are known for producing the crosslinked polymers. The crosslinking agents are low molecular weight compounds e.g. glutaraldehyde and epichlorohydrin. For a range of applications, the presence of residual unreacted or partly reacted crosslinking agent introduces a variety of problems in the manufacture and use of the polymers. The problems include the gradual leaching of the crosslinking agent from the polymer and the inactivation of ligands e.g. proteins in affinity separation systems.

The invention aims to overcome these problems by providing copolymers incorporating a monomer unit which can generate crosslinks without resort to added low molecular weight crosslinking agent.

More particularly, the invention provides a hydrophilic crosslinkable copolymer comprising monomer units derived from an ester of an ethylenically unsaturated carboxylic acid wherein the ester group contains a labile primary hydroxyl group and monomer units derived from a halohydroxyalkyl ester of an ethylenically unsaturated carboxylic acid.

The invention also provides a method of making a hydrophilic crosslinkable copolymer which method comprises forming a composition comprising an ester of an ethylenically unsaturated carboxylic acid wherein the ester group contains a labile primary hydroxyl group, a halohydroxyalkyl ester of an ethylenically unsaturated carboxylic acid and a polymerisation initiator and subjecting the composition to conditions which generate free radicals from the polymerisation initiator.

In another aspect, the invention provides an element for use in the removal of a chemical species from a fluid comprising a support coated with a layer of a copolymer of the invention.

A method of removing a chemical species from a fluid comprises contacting the fluid with a polymer of the invention having a ligand for the species bound thereto.

All polymers of the invention are expected to be of use in affinity separation systems because of the presence of the labile hydroxy group.

The labile hydroxy group-containing monomer units may be present in an amount up to 95 mole percent based on the polymer. Preferably, the monomer units represent the major monomer component of the copolymer and may be present in an amount from 60 to 95 mole percent, more preferably from 75 to 90 mole percent.

Preferred labile hydroxy group-containing monomers include hydroxyalkyl-containing monomers such as hydroxyalkyl acrylates and methacrylates. A particularly preferred monomer is hydroxyethyl methacrylate.

The halohydroxyalkyl ester monomer units enable the copolymer to be crosslinked. The amount of the units present in the copolymer will depend on the degree of crosslinking desired. The monomer units will normally be present as a minor component of the polymer, for example, in an amount from 5 to 40 mole percent, preferably from 10 to 25 mole percent.

In a preferred embodiment, the halohydroxyalkyl ester is an acrylate or a methacrylate.

Preferably, the halohydroxyalkyl group contains from 2 to 6, more preferably 3, carbon atoms and the halo and hydroxy substituents are on adjacent carbon atoms. The preferred halo substituent is a chloro substituent. The most preferred monomer is 3-chloro-2-hydroxypropyl methacrylate.

An improvement in the hydrophilicity of the copolymer may be achieved by the incorporation of additional monomer units derived from an ester of an ethylenically unsaturated carboxylic acid wherein the ester group is free of any groups capable of participating in hydrogen bonding e.g. hydroxyl groups.

Such monomer units are preferably present in an amount up to 45 mole percent, preferably from 1 to 10 mole percent.

Preferred monomers include alkyl acrylates and methacrylates with methyl methacrylate being particularly preferred.

An improvement in the non-specific adsorption characteristics of the copolymer may be achieved by the incorporation of a minor amount of additional ethylenically unsaturated monomer units which are capable of conferring a negative charge to the copolymer. In this way, the unwanted adsorption of material e.g. protein to the surface is reduced. The monomer is preferably present in an amount from 1 to 10 mole percent.

Preferred negative charge-conferring monomers contain an ionisable acid function and include ethylenically unsaturated carboxylic acids e.g. acrylic acid and methacrylic acid.

A particularly preferred crosslinkable copolymer of the invention comprises monomer units derived from hydroxyethyl methacrylate, 3-chloro-2-hydroxypropyl methacrylate, methyl methacrylate and methacrylic acid.

The copolymers of the invention may be synthesised by standard free radical polymerisation processes. For example, a solution of the appropriate monomers and thermal polymerisation initiator may be heated for a period of time sufficient to produce the copolymer e.g. at a temperature from 50° to 80° C. for from 0.5 to 30 hours. Preferably, polymerisation is carried out at a pH low enough to prevent premature crosslinking e.g. at a pH not greater than 2.

The molecular weight of the crosslinkable copolymers is not critical. Preferably, the molecular weight is such that the copolymer can be dissolved in a solvent, coated and subsequently crosslinked. A preferred range of molecular weight (Mw) based on measurements reported hereinafter is from $10^5$ to $10^6$.

The crosslinkable copolymer can be crosslinked at a pH which is sufficiently high to enable crosslinking to occur. The crosslinkable copolymer is preferably crosslinked in the presence of a base. Examples of suitable bases include tetraalkylammonium hydroxides and alkali metal alkoxides and hydroxides. Preferred bases include tetrabutylammonium hydroxide and tetramethylammonium hydroxide.

If the crosslinkable copolymer of the invention is to be coated on a support, it may be employed in the form of a coating composition comprising the copolymer dissolved in a solvent. Preferably, the composition further comprises a base. The coating composition is coated on the support prior to crosslinking. Crosslinking occurs when the coating is dried, preferably at an elevated temperature, thereby facilitating the manufacture of the coated support.

The crosslinked copolymer is suitable for use in the selective removal of a chemical species from a fluid e.g. for use in affinity chromatography. Such use is enabled by the presence of the labile primary hydroxyl groups in the crosslinked copolymer. A ligand which will interact with the species to be removed may be covalently coupled to the copolymer through the labile primary hydroxyl group. In some cases, coupling may occur directly through the hydroxyl group. Alternatively, the hydroxyl group may be activated by reaction with an activating agent before ligand coupling occurs. A variety of activating agents are described in the prior art.

The interaction between the ligand and the species to be removed may be predominantly chemical such as ion exchange or chelation, or it may be of a biochemical nature such as the formation of affinity complexes between biochemical molecules. When the interaction is reversible, the immobilised species can be recovered by elution.

The invention provides an element for use in the removal of a chemical species from a fluid comprising a support coated with a layer of a copolymer of the invention.

The element may be prepared by coating a support with a coating composition as described above and by drying the coated support, preferably at an elevated temperature.

The invention also provides a method of removing a chemical species from a fluid which method comprises contacting the fluid with a crosslinked polymer of the invention having a ligand for the species bound thereto.

The invention is illustrated, by way of example, in the accompanying schematic drawings wherein:

FIG. 3 is a longitudinal sectional view taken along line 2—2 of FIG. 2; and,

FIG. 4 is a transverse sectional view taken along lines 3—3 of FIG. 2.

Figure 1:
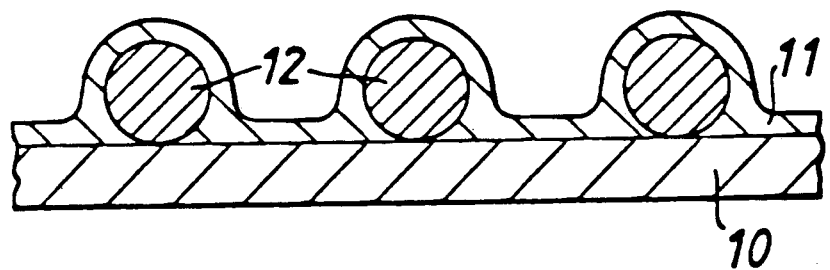
FIG. 1 is a cross sectional view of a preferred element of the invention.

The method may make use of biospecific affinity reactions and, in particular, immunochemical reactions. In this case, the ligand may be an immunochemical component e.g. a protein which exhibits biospecific affinity for another immunochemical component. An important class of such reactions is that between an antigen (or hapten) and an antibody directed against it. The use of monoclonal antibodies allows highly specific affinity reactions to be carried out.

Examples of antigens, commonly referred to as foreign substances, include viruses, bacteria, bacterial toxins, carbohydrates, hormones, drugs and lectins.

Specific examples of ligands which can be attached to the polymers of the invention include reactive dyes such as the triazine dyes Procion MX-R and Cibacron Blue F3G-A, a rat anti-mouse K-chain antibody and protein A.

When a ligand cannot be attached directly to the polymer, an activating agent may be used to permit coupling of the ligand. Examples of activating agents include divinyl sulphone, cyanogen bromide and carbonyl diimidazole.

The crosslinkable copolymers may be coated from solution. The coating solution may contain a base for crosslinking to occur. By the appropriate choice of base, crosslinking and thus manufacture can be controlled. For example, a base may be chosen so that crosslinking takes several hours before it is complete or heating may be required before effective crosslinking occurs.

The crosslinkable copolymer may be coated on a support and crosslinked to provide an element for use in the selective removal of a chemical species from a fluid e.g. for use in affinity chromatography.

The support may take the form of a sheet of material. The support sheet of the element of the invention may be formed from a variety of materials. For example, a suitable material may be a metal, glass or polymer. Many polymeric materials which can be formed into a sheet or film are suitable including, for example, cellulose ethers or esters e.g. cellulose acetate, polyesters e.g. poly(ethylene terephthalate), polyolefins e.g. poly(propylene) and poly(vinylchloride).

The thickness of the support may vary widely depending on the material from which it is made and on the way the element is used. For compactness, the support sheet is preferably as thin as possible while still meeting mechanical stability requirements. As an example, the thickness of the support sheet may be from 0.01 to 0.5 mm, more preferably from 0.05 to 0.2 mm.

Preferably, the support sheet is flexible. It is also preferred that the support sheet is flat.

Preferably, the polymer layer constitutes a continuous layer over the support.

The thickness of the polymer layer will depend upon such factors as the particular polymer employed. Since the interaction between the ligand and the species to be removed normally takes place predominantly at the surface of the layer, it need only be sufficiently thick to provide adequate attachment of the ligand to the support sheet. By way of example, the dry thickness of the polymer layer may be from 5 to 100 $\mu$m, more preferably from 10 to 50 $\mu$m.

Adequate adhesion between the polymer layer and the support sheet may be obtained by appropriate selection of the two materials involved. Alternatively, adhesion may be promoted by other means such as the use of a subbing layer or by subjecting the support sheet to a corona discharge or RF plasma treatment before applying the polymer layer.

A layer of the polymer may be provided on each side of the support sheet.

The polymer layer may contain particulate material which acts as spacer means i.e. the particulate material provides the means whereby an element of the invention can be spaced apart from another element or another part of the same element held against it. The particulate material may be held chemically on or within the polymer coating. Preferably, the particulate material comprises particles of substantially uniform shape and dimension. For many applications, it is desirable that the individual particles are distributed within the layer so as to provide a substantially uniform distance of separation between contiguous elements.

As described above, the particulate material may take a variety of forms including, for example, beads of polymer or glass. The dimension of the particles which determines the degree of spacing they provide will depend on such factors as the separation distance required between contiguous elements and the thickness of the polymer layer. Substantially spherical beads of an inert material all having substantially the same diameter within the range from 20 to 500 μm, preferably 30 to 200 μm, represent an example of a suitable particulate material.

A particularly advantageous feature of the particulate spacer means described above is that it is possible to coat the particulate material with the polymer layer. In this way, an element having integral spacer means is produced. By simply preparing a homogeneous coating composition from which the polymer layer is formed and the particulate material, the particles will be uniformly distributed over the coated layer thereby ensuring uniform separation.

The method for removing a chemical species from a fluid may be carried out in an apparatus comprising a housing defining a chamber, the housing having fluid inlet and outlet means, the chamber holding at least one element of the invention comprising a ligand for the species to be removed, the element or elements being positioned relative to the inlet and outlet to define a flow path such that, when the apparatus is in use, fluid entering the chamber through the inlet is passed over the surface of the element or elements before leaving the chamber through the outlet.

Preferably, the flow path is such that the depth of the fluid passing over the element or elements is from 20 to 500 μm, more preferably from 30 to 200 μm.

The element of the invention contained by the apparatus may be configured in a number of different ways.

For example, the apparatus may comprise a plurality of elements in face to face configuration, each element being separated from adjacent elements by spacer means.

In a preferred embodiment of the apparatus, the element is in the form of a coil wherein the convolutions of the coil are separated by spacer means and the defined flow path is axial relative to the axis of the coil.

In another preferred embodiment, the element is in the form of a coil wherein the convolutions of the coil are separated by spacer means and the defined flow path is circumferential through the convolutions.

Preferably, the spacer means provides a substantially constant separation distance between adjacent surfaces of the element or elements. The separation distance may be from 20 to 500 μm, preferably from 30 to 200 μm.

As described above, the spacer means may be integral with the element. Alternatively, the spacer means may be separate and take the form of, for example, tape, rods or a mesh-like structure which permit the flow of fluid through the apparatus.

When it is not important for the spacer means to provide a substantially uniform distance of separation, the spacer means may be the element itself. For example, the element may be corrugated and adjacent parts of it or adjacent separate elements arranged so that only parts of the element or elements are contiguous.

Advantages associated with the use of the apparatus described above include the fact that it is capable of handling fluids containing particulate materials e.g. cells and hence is very much less prone to blockage by such particulate material compared to available apparatus. Further, the apparatus is self-contained, and convenient to use and dispose of which makes it suitable for once only use if desired. This is an important consideration when handling materials containing substances such as pathogens, viruses or DNA products, or when the treated fluid is to be re-injected into a patient (e.g. bone marrow purging). Additionally, the apparatus is readily pre-packaged and, if desired, pre-sterilized.

It will be appreciated that the apparatus could be supplied in different forms having regard to the nature of the element contained therein. For example, the polymer layer could be in activatable form so that, before use, it would require treatment with an activating agent and subsequent treatment for binding the ligand. Alternatively, the polymer layer could already be activated and simply require treatment for binding the ligand. Finally, the apparatus could be supplied with ligand attached to the element.

The element and method of the invention are further described with reference to and as illustrated in FIGS. 1 to 4 (not to scale).

FIG. 1 shows a cross-sectional view of an element of the invention. The element comprises a support sheet 10 coated with a layer of a polymer of the invention 11. Beads 12 incorporated in the layer 11 adhere to the support 10.

Figure 2:
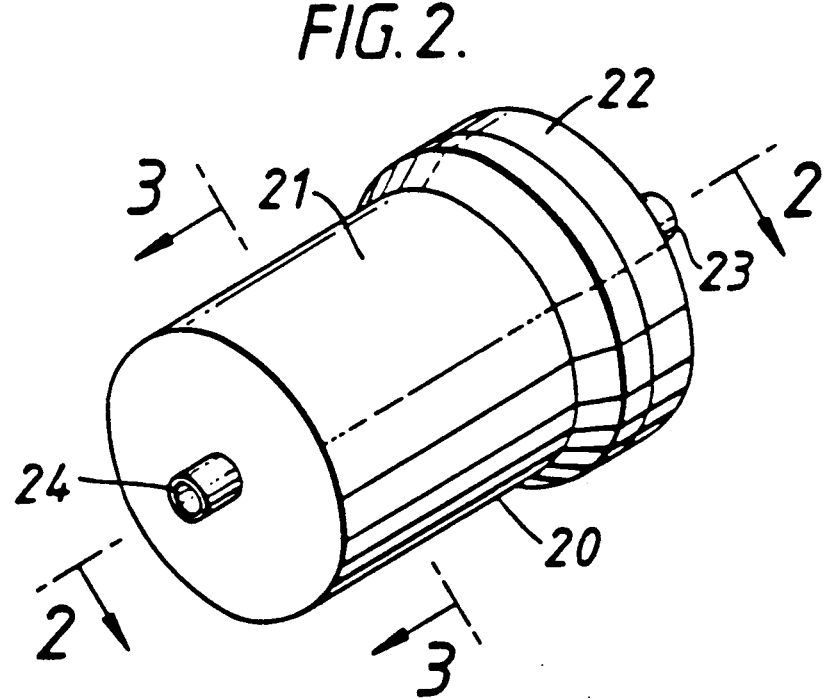
FIG. 2 is a perspective view of the exterior of an apparatus in which the element can be used.

FIG. 2 is a perspective view of the exterior of an apparatus in which the element can be used. The housing 20 is shown which may be moulded from a plastics material e.g. polypropylene. The housing 20 comprises a cylindrical body portion 21 to which is attached a lid 22. The lid is provided with fluid inlet tube 23 and the body portion is provided with a fluid outlet tube 24.

FIGS. 3 and 4 are sectional views taken along lines 2—2 and 3—3, respectively, of FIG. 2.

The lid 22 contains an axial passageway 25 through which fluid may be passed into the chamber defined by the housing 20. The inner surface of the lid 22 is provided with grooves 26 extending radially from the passageway 25 to spread the flow of fluid as it enters the chamber. The chamber contains a coil 27 of an element of the invention. An element of the type shown in FIG. 1 is helically wound on a cylindrical core 28. The outer winding of the coil is attached to the body of the coil by an adhesive tape 29 which is co-extensive with the outer surface of the coil and provides a fluid-tight seal between the coil and the inner surface of the housing 20.

The coil fills the chamber between the lid 22 at one end and a polypropylene disc 30 held against the circular wall of the chamber at the other end. The surface of the disc facing the coil is provided with grooves 31 extending radially from a central passageway running axially through the disc. This passageway communicates with the passageway 32 passing through the end wall of the housing and outlet tube 24.

When the apparatus is in use, fluid entering the chamber through the inlet passes axially through the convolutions of the coil before leaving the chamber through the outlet.

It is emphasized that the drawings and, in particular, the representation of the coil are schematic. In practice, the overall thickness of the element may be of the order of 200 μm. A coil may be produced from such an element in the form of a strip 35 mm wide and 11 m long helically wound on a central cylindrical core having a diameter of approximately 12 mm. Such a coil may be contained in an apparatus of the type shown having an overall length of 80 mm and an external diameter of 70 mm. Clearly, the coil consists of many closely-spaced convolutions which it would be impossible to show adequately in a scale drawing.

The invention is further described by way of example as follows.

EXAMPLE 1

Synthesis of poly (2-hydroxyethyl methacrylate-co-3-chloro-2-hydroxypropyl methacrylate) (9:1)

A 500 ml, 3-necked round bottomed flask was charged with the following:

| | |
|---|---|
| 2-hydroxyethyl methacrylate (0.43 moles) | 55.54 g |
| 3-chloro-2-hydroxypropyl methacrylate (0.048 moles) | 8.51 g |
| 2,2'-azobis(isobutyronitrile) | 0.1998 g |
| dioxan | 100 ml |
| nitric acid (conc) (pH = 2) | 0.2 ml |

The solution was stirred at 50° C. for 1.5 hours. Nitrogen was bubbled through the solution throughout this period. The polymer was recovered by precipitation into an excess of diethyl ether and dried in a dessicator. (Yield =5.25 g).

EXAMPLE 2

Synthesis of poly(2-hydroxyethyl methacrylate-co-3-chloro-2-hydroxypropyl methacrylate) (19:1)

A 500 ml, 3-necked round bottomed flask was charged with the following:

| | |
|---|---|
| 2-hydroxyethyl methacrylate (0.46 moles) | 60.00 g |
| 3-chloro-2-hydroxypropyl methacrylate (0.025 moles) | 4.38 g |
| 2,2'-azobis(isobutyronitrile) | 0.200 g |
| dioxan | 100 ml |
| nitric acid (conc) (pH = 2) | 0.2 ml |

The procedure of Example 1 was followed except that the reaction time was 4.0 hours. (Yield =3.48 g).

EXAMPLE 3

Synthesis of poly(2-hydroxypropyl methacrylate-co-3-chloro-2-hydroxypropyl methacrylate) (9:1)

A 100 ml, 3-necked round bottomed flask was charged with the following:

| | |
|---|---|
| 2-hydroxypropyl methacrylate (0.162 moles) | 23.40 g |
| 3-chloro-2-hydroxypropyl methacrylate (0.018 moles) | 3.23 g |
| 2,2'-azobis(isobutyronitrile) | 0.2017 g |
| dioxan | 30 ml |
| nitric acid (conc) (pH = 1) | 0.1 ml |

The procedure of Example 1 was followed. (Yield =3.32 g).

EXAMPLE 4

Synthesis of poly(2-hydroxyethyl methacrylate-co-methyl methacrylate-co-3-chloro-2-hydroxypropyl methacrylate) (36:3:1)

A 1000 ml, 3-necked round bottomed flask was charged with the following:

| | |
|---|---|
| 2-hydroxyethyl methacrylate (0.45 moles) | 58.50 g |
| Methyl methacrylate (0.0375 moles) | 3.75 g |
| 3-chloro-2-hydroxypropyl methacrylate (0.0125 moles) | 2.235 g |
| bis(4-tert. butylcyclohexyl)-peroxydicarbonate | 0.98 g |
| ethanol/methylcellosolve (9:1) | 500 ml |
| p-toluenesulphonic acid monohydrate (pH = 2) | 2.1 g |

The procedure of Example 1 was followed except that the reaction time was 17 hours. (Yield =39.45 g).

EXAMPLE 5

Synthesis of poly(2-hydroxyethyl methacrylate-co-methyl methacrylate-co-3-chloro-2-hydroxypropyl methacrylate) (90:9:1)

A 1000 ml, 3-necked round bottomed flask was charged with the following:

| | |
|---|---|
| 2-hydroxyethyl methacrylate (0.45 moles) | 58.50 g |
| Methyl methacrylate (0.045 moles) | 4.50 g |
| 3-chloro-2-hydroxypropyl methacrylate (0.005 moles) | 0.893 g |
| bis (4-tert. butylcyclohexyl)-peroxydicarbonate | 0.639 g |
| ethanol/methylcellosolve (9:1) | 250 ml |
| p-toluenesulphonic acid monohydrate (pH = 1-2) | 2.1 g |

The procedure of Example 1 was followed except that the reaction time was 24 hours. (Yield =57.58g).

EXAMPLE 6

Synthesis of poly(2-hydroxyethyl methacrylate-co-methyl methacrylate-co-3-chloro-2-hydroxypropyl methacrylate) (17:1:2)

A 1000 ml, 3-necked round bottomed flask was charged with the following:

| | |
|---|---|
| 2-hydroxyethyl methacrylate (0.85 moles) | 110.50 g |
| Methyl methacrylate (0.05 moles) | 5.00 g |
| 3-chloro-2-hydroxypropyl methacrylate (0.10 moles) | 17.88 g |
| bis (4-tert. butylcyclohexyl)-peroxydicarbonate | 1.334 g |
| ethanol/methylcellosolve (9:1) | 500 ml |
| p-toluenesulphonic acid monohydrate (pH = 1) | 4.2 g |

The procedure of Example 1 was followed except that the reaction time was 24 hours. (Yield =77.90g).

EXAMPLE 7

Synthesis of poly(2-hydroxyethyl methacrylate-co-methyl methacrylate-co-methacrylic acid-co-3-chloro-2-hydroxypropyl methacrylate) (40:3:3:9)

A 1000 ml, 3-necked round bottomed flask was charged with the following:

| | |
|---|---|
| 2-hydroxyethyl methacrylate (0.48 moles) | 62.45 g |
| Methyl methacrylate (0.036 moles) | 3.60 g |
| Methacrylic acid (0.036 moles) | 3.06 g |
| 3-chloro-2-hydroxypropyl methacrylate (0.108 moles) | 19.29 g |
| bis(4-tert. butylcyclohexyl)-peroxydicarbonate | 0.884 g |
| ethanol/methylcellosolve (9:1) | 250 ml |
| p-toluenesulphonic acid monohydrate (pH = 1-2) | 2.1 g |

The procedure of Example was followed except that the reaction time was 17 hours. (Yield =72.8g).

EXAMPLE 8

Synthesis of poly(2-hydroxyethyl methacrylate-co-methyl methacrylate-co-3-chloro-2-hydroxypropyl methacrylate) (18:1:1)

A 1000 ml, 3-necked round bottomed flask was charged with the following:

| | |
|---|---|
| 2-hydroxyethyl methacrylate (0.90 moles) | 117.0 g |
| Methyl methacrylate (0.05 moles) | 5.0 g |
| 3-chloro-2-hydroxypropyl methacrylate (0.05 moles) | 8.94 g |
| bis(4-tert. butylcyclohexyl)-peroxydicarbonate | 1.30 g |
| ethanol/methylcellosolve (9:1) | 500 ml |
| p-toluenesulphonic acid monohydrate (pH = 1) | 4.2 g |

The procedure of Example 1 was followed except that the reaction time was 23 hours. (Yield=52.34 g).

The molecular weight of the polymer was measured by gel permeation chromatography (GPC). A sample solution was prepared by dissolving 20 mg polymer in 10 ml solvent. 0.25 ml of 2% 1,2-dichlorobenzene was added to the solution as an internal marker. The sample was filtered through a 0.2 μm membrane filter before injection into the GPC system. Using dimethylformamide containing 100 ppm lithium bromide as the solvent, chromatography was carried out at a flow rate of 0.5 ml/min and at a temperature of 80° C. The detector measured refractive index (Knauer). The polymer was shown to have a weight average molecular weight (Mw) of 400,000. (The molecular weight obtained is expressed as a poly(ethylene glycol)/poly(ethylene oxide) equivalent, since the GPC system used was calibrated with a combination of poly(ethylene glycol) and poly(ethylene oxide).

The number average molecular weight (Mn) of the copolymer was found to be 33,900 making the polydispersity of the system 11.8.

Differential scanning calorimetry (DSC) showed that the Tg of the polymer was 127.2° C.

EXAMPLE 9

Synthesis of poly(2-hydroxyethyl methacrylate-co-methyl-methacrylate-co-methacrylic acid-co-3-chloro-2-hydroxypropyl methacrylate (16:1:1:2)

A one liter, 3-necked round bottom flask, fitted with a condenser and nitrogen inlet, was charged with the following:

| | |
|---|---|
| 2-hydroxyethyl methacrylate (0.48 moles) | 62.45 g |
| methyl methacrylate (0.03 moles) | 3.00 g |
| methacrylic acid (0.03 moles) | 2.55 g |
| 3-chloro-2-hydroxypropyl methacrylate (0.06 moles) | 10.72 g |
| p-toluenesulphonic acid monohydrate | 2.10 g |
| bis (4-tert.butylcyclohexyl)-peroxydicarbonate | 0.79 g |
| ethanol/methyl cellosolve (9:1 v/v) | 250 ml |

The procedure of Example 1 was followed except that the reaction time was 17 hours. (Yield=74.9 g).

A number of polymers of different molecular weight were prepared having the monomer composition described above. Molecular weights (Mw) measured by the method described in Example 8 varied from 250,000 to 409,000. Molecular weights (Mn) ranged from 29,600 to 79,500 and the range of polydispersity was from 3.14 to 11.9.

The polymers had glass transition temperatures (Tg) ranging from 97.1 to 115.2° C.

EXAMPLE 10

Polymer Coatings

For each of the polymers of Examples 1 to 8, a coating solution was prepared comprising 10% w/w of the polymer in 100% dimethylformamide plus 5% w/w potassium tertiary butoxide/polymer. The potassium tertiary butoxide was added in a tertiary butanol solution (10% w/w). 50 μm silica-coated styrene beads were incorporated in suspension in the solution as spacer beads.

The solution was coated on one side of a corona discharge treated polyethylene terephthalate sheet to provide a wet laydown thickness of 100 μm. The coating was dried at 90° C.

EXAMPLE 11

Polymer Coating

A coating solution was prepared consisting of 10% w/w of the polymer of Example 9 in 100% dimethylformamide plus 10% w/w tetrabutyl ammonium hydroxide/polymer. 100 μm silica-coated styrene beads were incorporated in suspension in the solution as spacer beads.

The solution was coated on one side of a corona discharge treated polyethylene terephthalate sheet to provide a wet laydown thickness of 100 μm. The coating was dried at 90° C. for about 20 minutes. The other side of the sheet was similarly coated except that the coating solution did not contain the spacer beads.

The coatings were stable in water, salt solutions, ethanol, acetone and dimethylformamide demonstrating that effective cross-linking had taken place.

EXAMPLE 12

Chromatographic Use

Samples of the coated polymer of Example 11 were activated by treatment with a 4% divinylsulphone solution in 0.5M sodium bicarbonate, pH 11. Rat anti-mouse K-chain monoclonal antibody at 0.8 mg/ml was coupled to the activated polymer coatings in 0.1M sodium bicarbonate, 0.5M sodium chloride solution at pH 8. The rat anti-mouse K-chain antibody was purified from ascites fluid obtained from Sera-lab (clone OX-20, code MAS 202C).

Jurkat cells, a human T-cell leukaemia (J. Experimental Medicine 152: 1709, 1980; Gillis, S., and Watson, J) grown in RPMI 1640 medium supplemented with 5% foetal calf serum (both from Flow Laboratories) were washed free of medium and resuspended in phosphate-buffered saline. (PBS composition: 0.15M NaCl, 2.7 mM KCl, 8 mM $Na_2HPO_4$, 1.5 mM $KH_2PO_4$, ph 7.2). The viability of the cells was greater than 85% as judged by trypan blue exclusion.

A total of $3.1 \times 10^7$ Jurkat cells ($5.2 \times 10^6$ cells/ml) were labelled with a mouse monoclonal antibody against the T cell surface antigen CD2. The antibody was obtained from Becton Dickinson Ltd., (Anti-Leu-5b, catalogue No. 7590). The antibody was added to the cells in the proportion 0.5 µg antibody/$10^7$ cells. Cells and antibody were incubated together, after which excess antibody was removed by centrifugation and the labelled cells resuspended in PBS.

The polymer coatings to which OX-20 was coupled were incubated with the suspension of the labelled cells. The coatings were subsequently washed with PBS and examined microscopically. The coatings showed a good even coverage of bound cells at high density.

For comparison, samples of the coating were incubated with non-antibody labelled cells. Subsequent microscopic examination revealed that virtually no cells had become bound to the polymer.

EXAMPLE 13

Chromatographic Use

A polymer-coated polyethylene terephthalate sheet was prepared as described in Example 11 except that 50 µm silica-coated styrene beads were used instead of the 100 µm size beads.

The coated sheet was slit into strips approximately 15 m long and 35 mm wide. A strip was spooled under clean conditions onto a central core and the coiled element was inserted into an apparatus similar to that shown in FIGS. 2-4 made of polypropylene. After inserting the coiled element into the body of the apparatus, the lid was attached by ultrasonic welding.

The apparatus was flushed with "Millipore" quality water.

Cibacron Blue F3G-A dye was coupled to the coiled element in accordance with the following procedure. 2.4 g of dye dissolved in 65 ml water and 10 ml sodium chloride solution (4M) was pumped through the previously flushed apparatus at 60 ml/min for 30 mins. The apparatus was left standing for 90 mins at room temperature to allow the dye to adsorb to the polymer surface.

1.25 ml of sodium hydroxide solution (10M) was added to the dye solution which was circulated through the apparatus for 30 mins at a pH greater than 12. The inlet and outlet ports of the apparatus were sealed and it was stored in a shaker at 25° C. for two days.

Water was flushed through the apparatus at 60 ml/min until no dye was detected by spectral absorption at 280 nm. Any uncoupled dye was removed from the coating surface by flushing with sodium chloride (1M)/ethyl alcohol (25%) solution.

The apparatus was flushed with 200 ml 0.05 M phosphate buffer solution (pH 7) at 50 ml/min. 50 ml untreated rabbit serum was loaded into the apparatus at 30 ml/min. The first 30 ml solution leaving the apparatus was discarded and the remaining solution was circulated through the apparatus for 30 mins at the same flowrate. The pump was then switched off and the apparatus was left standing for a further 30 mins. 0.05 M phosphate buffer solution was flushed through the apparatus at 60 ml/min until UV absorption at 280 nm of the washings was zero.

Elution was carried out with a chosen solution at 30 ml/min and the first six fractions collected. The solution was circulated at 30 ml/min for 10 mins and a seventh fraction was collected. The flowrate was increased to 60 ml/min and a further $2 \times 20$ ml fractions were collected.

Using 0.2 M NaSCN/0.05 M Tris/HCl (pH 8) as the eluent for a number of runs yielded 3-11 mg albumin.

Protein recovery was determined by optical absorption at 280 nm and electrophoresis was used to identify the recovered protein.

Protein recovery has also been demonstrated using Procion MX-R dye instead of Cibacron F3G-A following the procedure of this Example.

We claim:

1. A hydrophilic crosslinkable copolymer comprising monomer units derived from an ester of an ethylenically unsaturated carboxylic acid wherein the ester group contains a labile primary hydroxyl group and monomer units derived from a halohydroxyalkyl ester of an ethylenically unsaturated carboxylic acid.

2. A copolymer according to claim 1 wherein the labile hydroxy group-containing monomer units are present in an amount from 60 to 95 mole percent.

3. A copolymer according to claim 1 or claim 2 wherein the labile hydroxy group-containing monomer is a hydroxyalkyl acrylate or methacrylate 4. A copolymer according to claim 3 wherein the labile hydroxy group-containing monomer is hydroxyethyl methacrylate.

5. A method of making a hydrophilic crosslinkable copolymer which method comprises forming a composition comprising an ester of an ethylenically unsaturated carboxylic acid wherein the ester group contains a labile primary hydroxyl group, a halohydroxyalkyl ester of an ethylenically unsaturated carboxylic acid and a polymerisation initiator and subjecting the composition to conditions which generate free radicals from the polymerisation initiator.

* * * * *